United States Patent [19]
Teirstein et al.

[11] Patent Number: 6,059,748
[45] Date of Patent: *May 9, 2000

[54] CATHETERS WITH ENHANCED EXCHANGE CAPABILITY

[75] Inventors: Paul Teirstein, La Jolla; Brett Trauthen, Newport Beach; Mark Hall, Yorba Linda, all of Calif.

[73] Assignee: Advanced Cardiovascular Systems, Inc., Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/966,849

[22] Filed: Nov. 7, 1997

Related U.S. Application Data

[63] Continuation of application No. 08/464,328, Jun. 5, 1995, abandoned.

[51] Int. Cl.$^7$ ................................................ A61M 31/00
[52] U.S. Cl. ......................... 604/53; 604/158; 604/164; 604/28; 604/264
[58] Field of Search ............................ 604/28, 99, 52–3, 604/93, 96, 158, 160–1, 163–6, 171, 263.4, 272, 280, 283; 606/191, 194

[56] References Cited

U.S. PATENT DOCUMENTS

| | | | |
|---|---|---|---|
| 4,449,532 | 5/1984 | Storz | 606/191 |
| 4,862,891 | 9/1989 | Smith | 606/191 |
| 4,994,027 | 2/1991 | Farrell | 604/53 |
| 5,290,241 | 3/1994 | Kraus et al. | 604/158 |
| 5,324,269 | 6/1994 | Miraki | 604/160 |
| 5,417,669 | 5/1995 | Castaneda et al. | 604/160 |
| 5,449,362 | 9/1995 | Chaisson et al. | 606/108 |
| 5,458,613 | 10/1995 | Gharibadeh et al. | 604/96 |
| 5,498,240 | 3/1996 | Bagaoisan et al. | 604/283 |
| 5,501,227 | 3/1996 | Yock | 128/673 |
| 5,507,731 | 4/1996 | Hernandez et al. | 604/283 |
| 5,507,732 | 4/1996 | McClure et al. | 604/283 |
| 5,516,336 | 5/1996 | McInnes | 604/96 |
| 5,549,554 | 8/1996 | Miraki | 604/53 |

FOREIGN PATENT DOCUMENTS

| | | |
|---|---|---|
| 4208912 C1 | 5/1993 | Germany . |
| 93 15 610 U | 3/1994 | Germany . |
| WO92/15357 | 9/1992 | WIPO . |

*Primary Examiner*—Wynn Wood Coggins
*Assistant Examiner*—Jennifer R. Sadula
*Attorney, Agent, or Firm*—Heller Ehrman White & McAuliffe LLP

[57] ABSTRACT

An exchange catheter facilitates the replacement of an existing guiding catheter with a larger guiding catheter during catheterization procedures such as percutaneous transluminal coronary angioplasty without disturbing the position of a guidewire. The exchange catheter has a distal portion through which a guidewire is slidable. The outer diameter of the distal portion is slightly less than the inner diameter of the existing guiding catheter. A femoral sheath is slidable over the proximal portion of the exchange catheter so as to facilitate femoral sheath exchange.

18 Claims, 4 Drawing Sheets

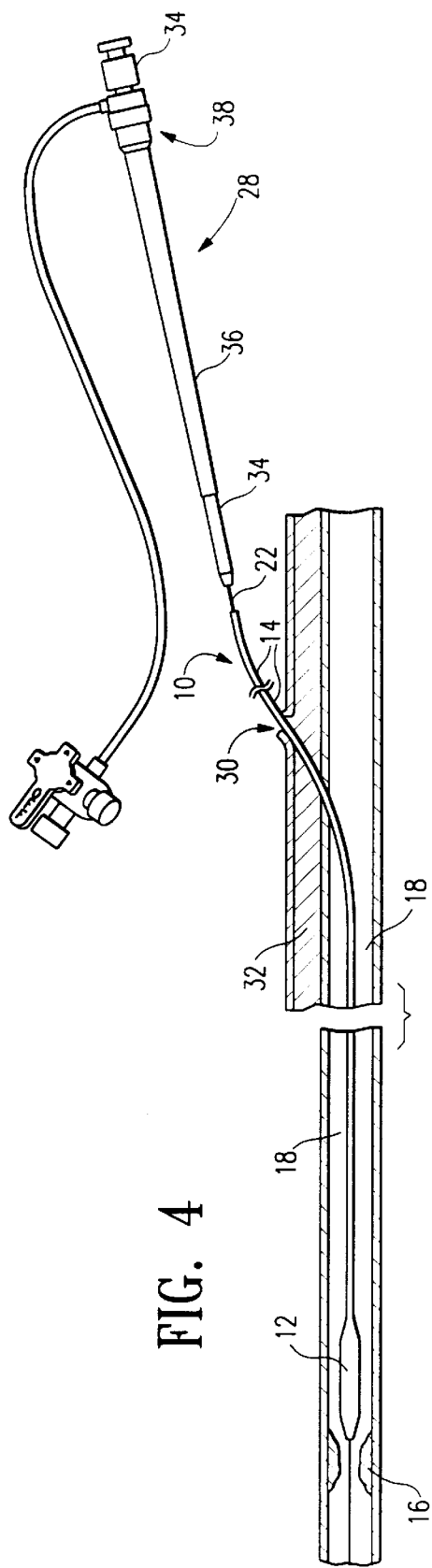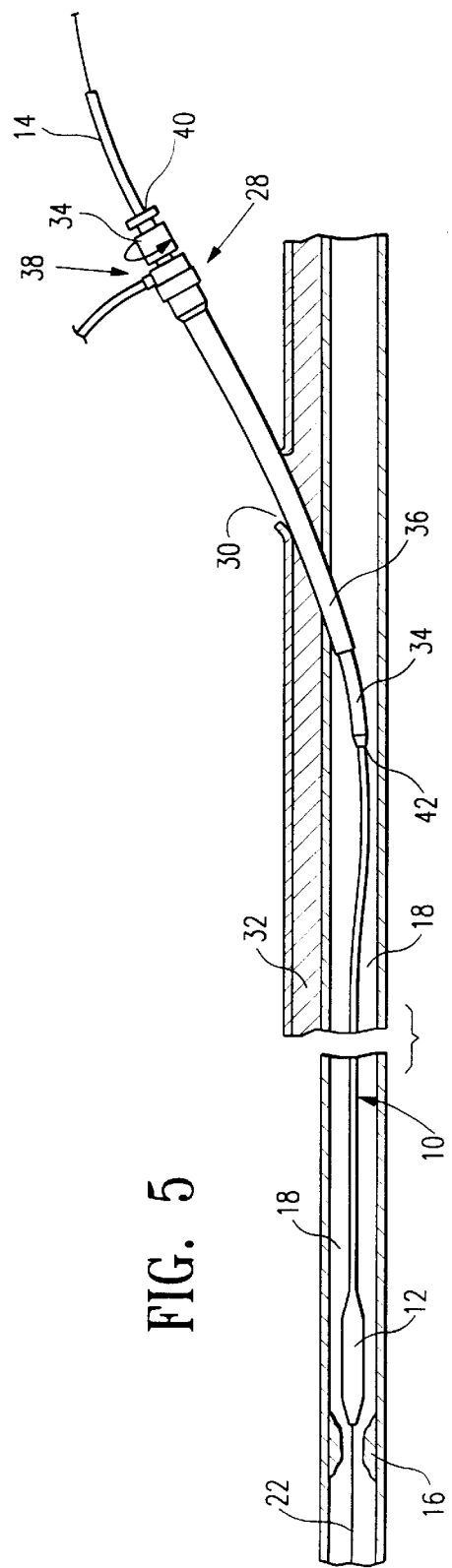

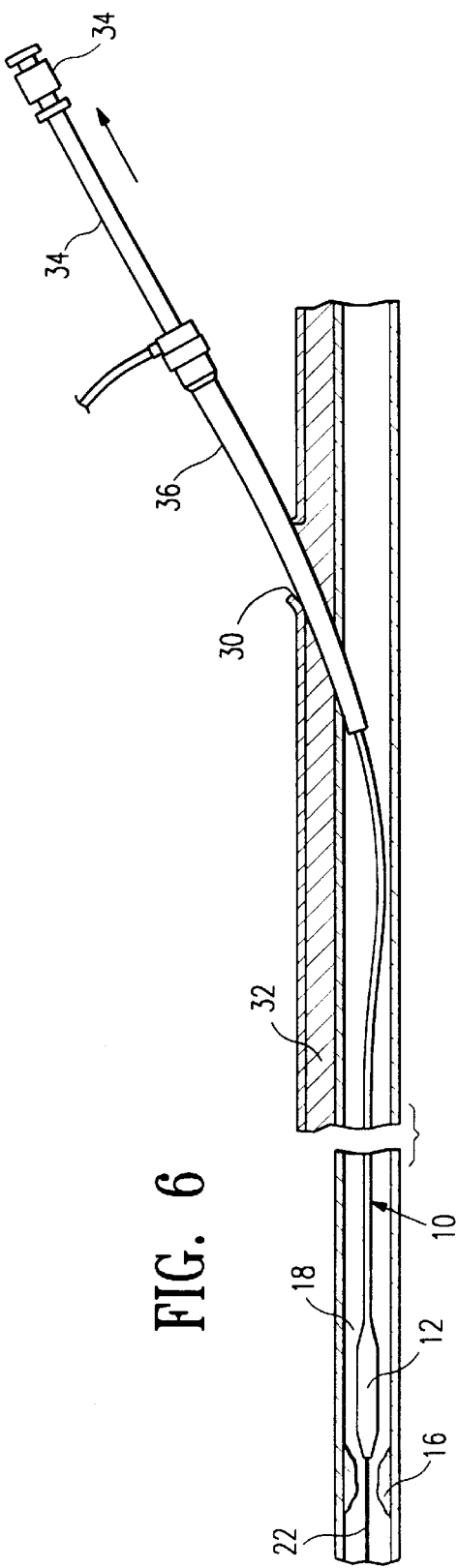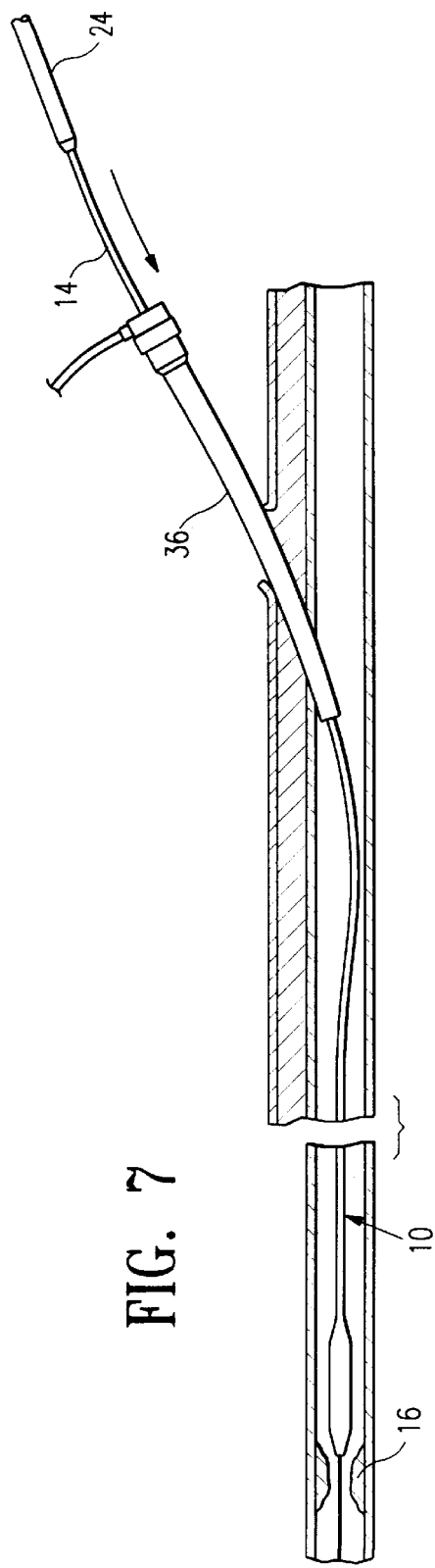

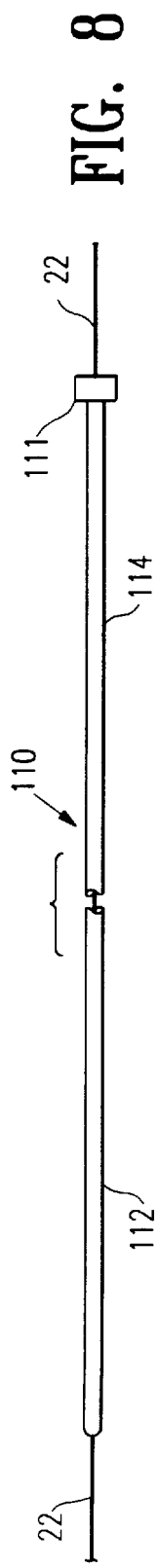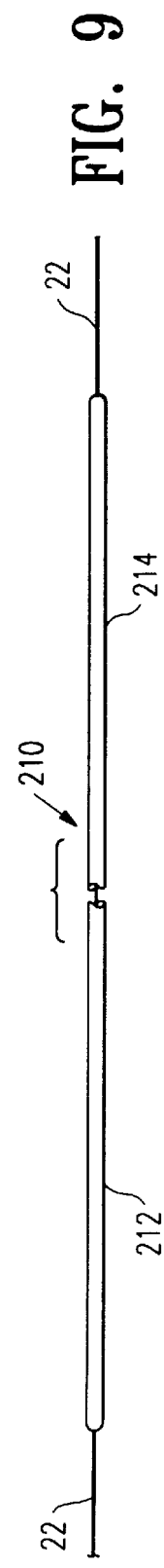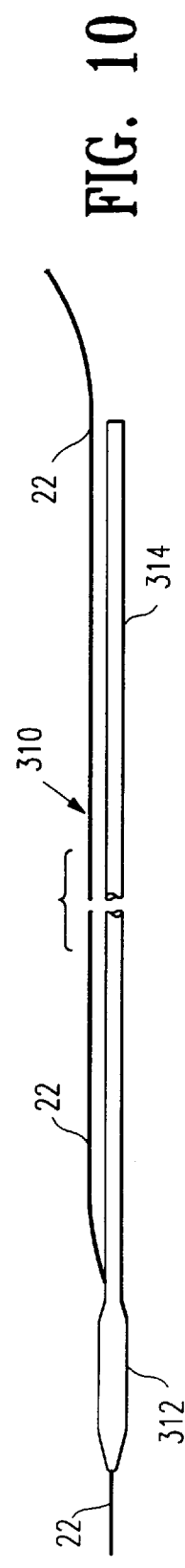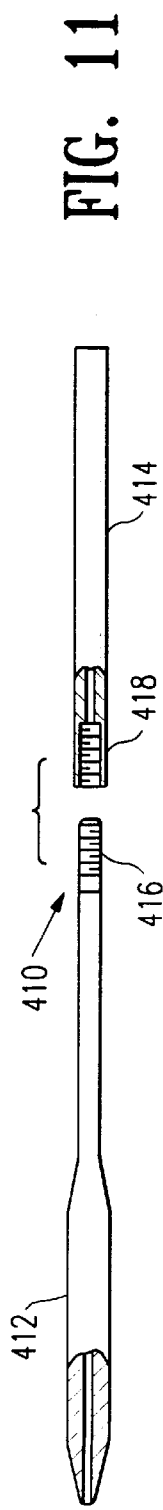

CATHETERS WITH ENHANCED EXCHANGE CAPABILITY

This is a continuation of application Ser. No. 08/464,328, filed on Jun. 5, 1995 now abandoned.

BACKGROUND OF THE INVENTION

1. Field of the Invention

The present invention relates to exchange catheters for facilitating the exchange of a guiding catheters during catheterization procedures without disturbing the position of a guidewire. More particularly, the present invention relates to such exchange catheters which further facilitate the exchange of femoral sheaths.

2. Description of the Related Art

Catheterization procedures are the foundation of percutaneous transluminal coronary angioplasty (PTCA), which is a procedure used in the treatment of obstructive disorders of the human vascular system. Briefly, PTCA entails inserting a long, tubular guiding catheter through the skin (percutaneous) of a patient into a blood vessel, most commonly the femoral artery, with the aid of an introducer and a femoral sheath. The guiding catheter is advanced through the artery (transluminal) to a point at which the far or distal end of the guiding catheter is positioned near an obstruction or stenotic lesion in a blood vessel of the heart (coronary). A guidewire is then inserted though the guiding catheter, exiting out a port in the guiding catheter distal end, and is advanced through the lesion. An interventional device such as a balloon catheter is then inserted through the guiding catheter over the guidewire to treat the lesion (angioplasty).

During PTCA, in order to minimize trauma to the patient, the guiding catheter and, accordingly, the interventional device should be as small as possible while still being able to treat the lesion. However, it may be determined during PTCA that a larger interventional device is needed to perform the angioplasty successfully. Therefore, the guiding catheter may need to be replaced with a larger guiding catheter which is able to accommodate a larger interventional device. However, this exchange of guiding catheters must take place most preferably without disturbing the position of the guidewire within or displacing the guidewire from the stenotic lesion. Additionally, if the guidewire is inadvertently pulled out of or displaced from the stenotic lesion so that the guidewire would need to be advanced through the stenotic lesion again to continue the angioplasty, traumatic complications may occur, with the only option being emergency surgery which is known to have higher morbidity and mortality rates. This is particularly true if the initial treatment caused vessel spasm or abrupt closure of the blood vessel at the stenotic lesion.

Numerous techniques have been developed for the exchange of guiding catheters while attempting not to disturb the position of the guidewire within the stenotic lesion. Although many of these techniques address the maintenance of guidewire position, they do not address more specific areas of concern, e.g., femoral sheath exchange capability or supportive configurations for facilitating catheter exchange.

Accordingly, due to the delicate nature of catheterization procedures there is a need in the art of exchange catheters for an exchange catheter which facilitates the exchange of one guiding catheter with a larger guiding catheter without disturbing the position of a guidewire within a stenotic lesion. Furthermore, there is a need in the art of exchange catheters for an exchange catheter which also facilitates the exchange of femoral sheaths so as to minimize trauma to a patient and to improve the success of catheterization procedures.

SUMMARY OF THE INVENTION

The exchange catheters of the present invention facilitate not only the exchange of one guiding catheter already positioned within a blood vessel of a patient with a different-sized guiding catheter in order to introduce an alternative interventional device, but also the exchange of femoral sheaths. In either situation the exchange is accomplished without disturbing the position of a guidewire within a stenotic lesion.

The exchange catheters generally comprise a flexible body with a distal portion positionable near a lesion in a blood vessel and a proximal portion receivable inside the blood vessel and extending outside the body of a patient when the distal portion is positioned near the lesion. In this manner the proximal portion is capable of manipulation by a physician to indirectly manipulate the distal portion. The exchange catheter has a lumen formed therein and an aperture formed in the end of the distal portion thereof such that a guidewire is slidable therethrough. The exchange catheter is slidably insertable over a guidewire and into a primary guiding catheter positioned in a blood vessel. It also is slidably removable from a subsequent or secondary guiding catheter positioned in the blood vessel and will do so without disturbing the position of the guidewire within the stenotic lesion. The guidewire is securable to the proximal portion of the exchange catheter so that the movement the guidewire is controllable as the primary guiding catheter slides over the exchange catheter and is removed from the blood vessel. Similarly, when the secondary guiding catheter slides over the exchange catheter and is inserted into the blood vessel over the exchange catheter, the guidewire position is controlled.

According to one aspect of the present invention, a femoral sheath is receivable on the proximal portion of the exchange catheter. As such, unlike prior art devices the exchange catheters of the present invention facilitate the exchange of femoral sheaths so that a larger guiding catheter may be inserted over the exchange catheter.

Another novel aspect of the present invention is that the distal portion has an outer diameter slightly less than the inner diameter of a primary guiding catheter being replaced. Therefore, the distal portion provides as much supportive guidance as possible to the replacement or secondary guiding catheter as it is being inserted over the exchange catheter, particularly in the aortic regions of the vascular system.

Additional aspects and novel features of the present invention will become apparent to those skilled in the art upon examination of the following detailed description with reference to the accompanying drawings.

BRIEF DESCRIPTION OF THE PREFERRED EMBODIMENTS

FIG. 4 is a perspective view of a catheter introducer and an exchange catheter illustrating the principles of the present invention;

FIG. 5 is a partial cross-sectional view of a catheter introducer and an exemplary exchange catheter;

FIG. 6 is a view similar to FIG. 5, particularly showing the removal of a femoral sheath;

FIG. 7 is another view similar to FIG. 5, particularly showing the insertion of a replacement guiding catheter;

FIG. 8 is a cross-sectional view of an exchange catheter with a securing device according to another embodiment of the present invention;

FIG. 9 is a side view of an exchange catheter according to yet another embodiment of the invention; and FIG. 10 is a side view of an exchange catheter according to still another embodiment of the present invention;

FIG. 11 is an elevational view, partially in section, of an exchange catheter having releasably connected shaft sections.

DETAILED DESCRIPTION OF THE PREFERRED EMBODIMENTS

Figure 1:
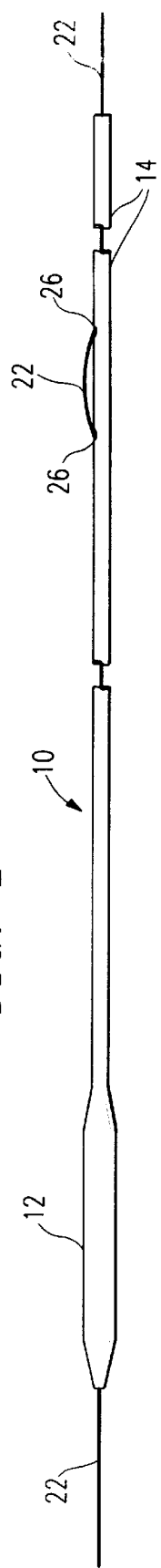
FIG. 1 is a side view of an exchange catheter according to an exemplary embodiment of the present invention.

Referring to the drawings, particularly to FIG. 1, an exemplary embodiment of an exchange catheter 10 according to the present invention is shown. The exchange catheter 10 facilitates the exchange of guiding catheters during catheterization procedures such as percutaneous transluminal coronary angioplasty (PTCA) without traumatically disturbing the position of an existing guidewire. The exchange catheter 10 generally comprises a flexible, cylindrical, elongate body having a distal portion 12 and a proximal portion 14. The distal and proximal portions 12 and 14 are defined, respectively, as the portions of the exchange catheter 10 farthest and nearest a physician performing the PTCA. The exchange catheter 10 may be a continuous tube in that the distal and the proximal portion 12 and 14 thereof are adjacent to each other.

Figure 2:
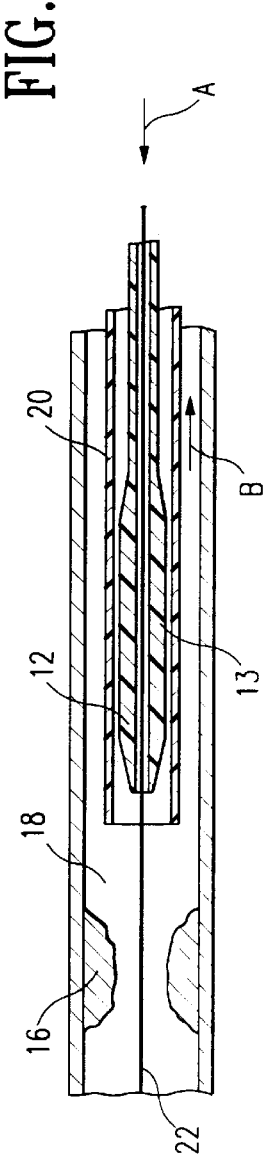
FIG. 2 is a cross-sectional view of the exchange catheter positioned within a blood vessel with a primary guiding catheter.

With additional reference to FIG. 2, when it is determined during PTCA that a different interventional device such as a balloon catheter (not shown) is required to treat more properly a stenotic lesion 16 of a blood vessel 18, a guiding catheter 20 positioned within the blood vessel 18 near the stenotic lesion 16 must be replaced without disturbing the position of a guidewire 22 received in the guiding catheter 20. (For clarity in the description hereunder, the guiding catheter 20 is designated as the "primary" guiding catheter.) In order to replace the primary guiding catheter 20, the exchange catheter 10 is inserted over the guidewire 22 and through the lumen of the primary guiding catheter 20, as shown by arrow A. The exchange catheter 10 is advanced through the primary guiding catheter 20 to a point where the distal portion 12 of the exchange catheter 10 is positioned near the stenotic lesion 16. As known in the art, the guidewire 22 is secured to the exchange catheter 10 at the proximal portion 14 thereof. The primary guiding catheter 20 is now removed from the blood vessel 18 by sliding the primary guiding catheter 20 over the exchange catheter 10, as shown by arrow B.

Accordingly, as the guidewire 22 is positioned within the exchange catheter 10 (exiting therefrom through an aperture formed in the tip thereof), the guidewire 22 is essentially shielded from the primary guiding catheter 20, so that as the primary guiding catheter 20 is removed from the blood vessel 18, the guidewire 22 is essentially undisturbed, particularly from any pulling action which may urge or displace the guidewire 22 from the stenotic lesion 16.

Figure 3:
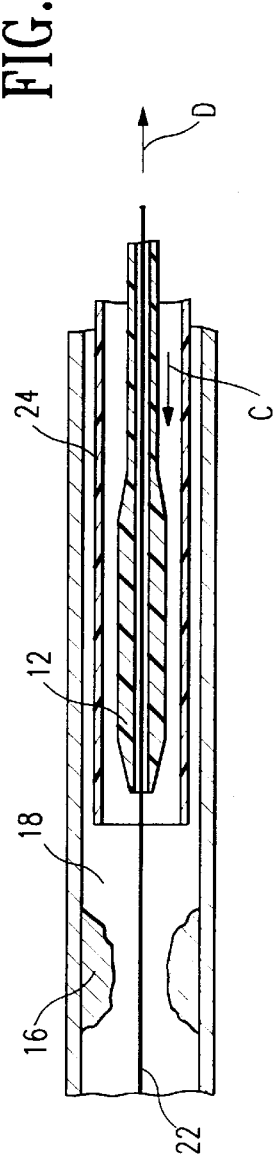
FIG. 3 is a cross-sectional view of the exchange catheter positioned within a blood vessel with a secondary guiding catheter.

With additional reference to FIG. 3, a replacement or "secondary" guiding catheter 24 is now inserted over the exchange catheter 10 and advanced to a point where the distal end of the secondary guiding catheter 24 is positioned near the stenotic lesion 16, as shown by arrow C. In the exemplary embodiment shown, the secondary guiding catheter 24 is of different size, e.g., larger, than the primary guiding catheter 20. As mentioned above, the guidewire 22 is essentially shielded from the secondary guiding catheter 24 by the exchange catheter 10. The exchange catheter 10 may now be removed from the blood vessel 18 by sliding the exchange catheter 10 over the guidewire 22 and through the secondary guiding catheter 24, as shown by arrow D. An alternative interventional device (not shown) may now be inserted over the guidewire 22 and through the secondary guiding catheter 24 to treat the stenotic lesion 16 as desired.

As is known in the art of exchange catheters, prior to inserting the exchange catheter 10 into the primary guiding catheter 20, the guidewire 22 is secured so that the insertion of the exchange catheter 10 does not disturb the position of the guidewire 22 within the lumen of the stenotic lesion 16. Additionally, the guidewire 22 is securable to the exchange catheter 10 so that the position of the guidewire 22 is not disturbed within or displaced from the stenotic lesion 16 as the primary and the secondary guiding catheter 20 and 24 are respectively removed and inserted into the blood vessel 18. In order to receive the guidewire 22, the exchange catheter 10 has an inner diameter of preferably approximately 0.020 inch, which is sufficient to receive commercially available guidewires having, for example, a diameter of 0.018 inch or less. Further, the inner diameter and the outer diameter of the secondary guiding catheter 24 are larger than those of the primary guiding catheter 20 so that a larger interventional device may be inserted in the blood vessel 18.

The outer diameter of the exchange catheter 10 is less than the inner diameter of the primary and secondary exchange catheters 20 and 24. More specifically, the outer diameter of the distal portion 12 of the exchange catheter 10 is slightly less than the inner diameter of the primary guiding catheter 20, such that the difference between the outer diameter of the distal portion 12 and the inner diameter of the primary guiding catheter 20 is relatively small or negligible. By having this relationship, the distal portion 12 of the exchange catheter 10 provides as much support or supportive guidance as possible for the secondary guiding catheter 24 as the secondary guiding catheter 24 is being inserted into the blood vessel 18, while still being insertable through the primary guiding catheter 20. This support facilitates as much as possible the insertion of the secondary guiding catheter 24 in the aortic region where the blood vessel 18 may have numerous turns and bends through which the catheters 10, 20, and 24 must advance. Preferably, the distal portion 12 of the exchange catheter 10 has an 4-French outer diameter or an outer diameter of approximately 0.052 inch.

In addition, as the distal portion 12 of the exchange catheter 10 may be advanced through more pronounced turns and bends in the blood vessel 18 than the proximal portion 14, it is preferable that the distal portion 12 be more flexible than the proximal portion 14. This is also preferable as the proximal portion 14 may need to be more stiff in order to advance the distal portion 12 through contorted bends which may impose resistance.

In relation to this, the length of the distal portion 12 is sufficient so that support may be provided within the coronary arteries and the descending aorta in the aortic region. For a typical human, the length of the distal portion 12 should be approximately 20 inches. (Note: For the sake of graphical clarity, FIGS. 2 and 3 do not show these dimensions proportionally.) Regarding the overall length of the exchange catheter 10, as PTCA most commonly uses the femoral artery as access to the coronary region (with the insertion originating in the thigh area), the length of the exchange catheter 10 must be adequate in order for the distal portion 12 to be positionable in the coronary or aortic region while the proximal portion 14 extends from the femoral artery to outside the body of the patient for manipulation by a physician; therefore, taking into consideration the dimensions of the human body, the overall length of the exchange catheter 10 should be approximately 100 inches.

With further reference to FIG. 1, in the exemplary embodiment shown, there may be at least one guidewire access port 26 formed in the proximal portion 14 of the exchange catheter 10. The access ports 26 allow the guidewire 22 to exit therethrough in a "monorail"-like fashion. The guidewire access ports 26 provide a physician access to the guidewire 22 during PTCA and exchange procedures, allowing greater or more versatile manipulation of the guidewire 22 than would be possible otherwise and facilitating femoral sheath exchange, which will be discussed below. Moreover, in order to provide easy manipulation for a physician, the guidewire access ports 26 are preferably spaced approximately 30 inches from the most proximal end of the exchange catheter 10.

The outer diameter of the proximal portion 14 of the exchange catheter 10 is large enough so that the inner diameter thereof is sufficient for the guidewire 22 to slide therethrough, yet small enough so that the exchange catheter 10 is capable of femoral sheath exchange. That is, the outer diameter of the proximal portion 14 may be generally less than the outer diameter of the distal portion 12. As shown in FIGS. 1 and 2, the distal portion 12 has a radially enlarged section 13 with a wall thickness and an outer diamemeter greater than the proximal portion 14. Preferably, the proximal portion 14 has an outer diameter of approximately 0.04 inch or of specifically 0.038 inch so that the exchange catheter 10 facilitates the exchange of commercially available femoral sheaths.

Referencing FIG. 4, a preferred embodiment of the exchange catheter 10 of the present invention is shown in systematic relation to a femoral sheath introducer 28. The femoral sheath introducer 28 is employed in PTCA to minimize trauma to the patient at the insertion site and to facilitate the insertion of the various catheters and devices used to perform the procedure. The exchange catheter 10 is shown inserted through an opening 30 of the skin 32 of a patient and into the blood vessel 18 with the distal end 12 thereof positioned near the stenotic lesion 16 and with the guidewire 22 positioned through the stenotic lesion 16. As shown in FIG. 4, the primary guiding catheter 20 has been removed, and the secondary guiding catheter 24 has yet to be inserted (cf. FIGS. 2 and 3). A femoral sheath introducer which was used in the introduction of the primary guiding catheter 20 into the blood vessel 18 is assumed to have been removed, also.

As discussed above, during PTCA when a physician decides that a larger or an alternative device is needed to successfully carry out the procedure, a larger guiding catheter, i.e., the secondary guiding catheter 24, may need to be employed. However, the outer diameter of the secondary guiding catheter 24 may be too large to be insertable into the catheter introducer which was used to introduce the primary guiding catheter 20 into the blood vessel 18. Therefore, a larger femoral sheath introducer, i.e., the femoral sheath introducer 28, will need to be used to introduce the secondary guiding catheter 24 into the blood vessel 18. An example of such a guiding catheter exchange may be from a 7-French guiding catheter to an 8-French guiding catheter.

The femoral sheath introducer 28 generally comprises a tubular dilator 34 and a tubular femoral sheath 36. The dilator 34 is slidably receivable within the sheath 36 and projects out both ends thereof. The proximal portion 14 of the exchange catheter 10 is slidably receivable within the dilator 34, that is, the exchange catheter 10 allows the dilator 34 to be placed or positioned on the proximal portion 14 thereof. A securing mechanism 38 is provided which prevents movement of the dilator 34 within the sheath 36 when the proximal portion 14 of the exchange catheter 10 (with the guidewire 22) is being advanced through the dilator 34.

With additional reference to FIG. 5, the exchange catheter 10 is inserted into the dilator 34 of the femoral sheath introducer 28, with the dilator introducer 28 advanced over the exchange catheter 10 and inserted into the opening 30 of the skin 32. The dilator 34 and the sheath 36 are both positionable in the blood vessel 18, and the proximal portion 14 of the exchange catheter 10 extends out of a rear port 40 of the dilator 34. Additionally, a tip 42 of the dilator 34 is tapered to facilitate the insertion of the femoral sheath introducer 28 into the blood vessel 18.

Referencing FIG. 6, after the femoral sheath introducer 28 has been inserted into the blood vessel 18, the securing mechanism 38 is actuated to release the dilator 34. The dilator 34 is then removed from the sheath 36 as shown by the arrow. With additional reference to FIG. 7, after the dilator 34 has been removed from the sheath 36, the secondary guiding catheter 24 is then inserted over the proximal portion 14 of the exchange catheter 10 and through the lumen of the sheath 36 and advanced over the exchange catheter 10 as discussed above with reference to FIG. 3. Accordingly, the inner diameter of the sheath 36 is sufficiently large to allow the secondary guiding catheter 24 to be inserted therethrough. As such, the sheath 36 has preferably an 8-French to 10-French inner diameter.

With reference to FIG. 8, an exchange catheter 110 according to another embodiment of the present invention is shown. The exchange catheter 110 generally comprises a flexible, tubular elongate body with a distal portion 112 and a proximal portion 114. A pin vise 111, which comprises a collar and a collet, is provided to secure the guidewire 22 to the proximal portion 114 of the exchange catheter 110 at a proximal end thereof. The provision of the pin vise 111 aids the physician during the exchange sequence in maintaining the position of the guidewire 22 within the stenotic lesion 16. Furthermore, the overall length of the exchange catheter 110 may be shortened with the provision of the pin vise 111 so that the exchange catheter 110 is substantially shorter than conventional exchange catheters. This may allow the proximal portion 114 to extend only a short distance outside the body of the patient relative to conventional exchange catheters. For the exemplary embodiment described, the pin vise 111 is preferably a 4-French pin vise, and the overall length of the exchange catheter 110 is approximately 50 inches. However, the pin vise 111 needs to be no larger in diameter than 0.038 inch to allow passage of the of the dilator over the pin vice 111.

Referencing FIG. 9, an exchange catheter 210 according to yet another embodiment of the invention is shown. In this exemplary embodiment, the exchange catheter 210 generally comprises a flexible, cylindrical, elongate body having a distal portion 212 and a proximal portion 214. The distal portion 212 and the proximal portion 214 have substantially equal outer diameters, preferably approximately 0.038 inch. Further, the inner diameter of the exchange catheter 210 is preferably substantially constant, with the guidewire 22 exiting the exchange catheter 210 at ends thereof. Moreover, the tip of the distal portion 212 should be atraumatic, i.e., designed so as not to harm or damage the blood vessel 18.

One advantage of the exchange catheter 210 is that it is relatively easy to manufacture.

In reference to FIG. 10, an exchange catheter 310 according to still another embodiment of the invention is shown. The exchange catheter 310 generally comprises a flexible, cylindrical, elongate body having a distal portion 312 and a proximal portion 314. In this embodiment, the proximal portion 314 does not have a lumen formed therein, in that the guidewire 22 is only slidable through the distal portion 312. As the proximal portion 314 is solid, it may by formed with a relatively small outer diameter while still urging the distal portion 312 through the primary guiding catheter 20. Accordingly, the preferable outer diameter of the proximal portion 314 is 0.020 inch. Further, it has been determined that the proximal portion 314 alongside a 0.014-inch guidewire is able to pass through an 8-French femoral sheath introducer. Also, as the proximal portion 314 does not have a lumen, the exchange catheter 310 is relatively easy to manufacture.

Yet another exemplary embodiment of the invention is shown in FIG. 11. An exchange catheter 410 generally comprises a flexible, cylindrical elongate body having two separate portions: a distal portion 412 and a proximal portion 414. A turnbuckle-type coupling mechanism releasably attaches the two portions 412 and 414 together and includes a threaded male portion 416 preferably disposed on the proximal end of the distal portion 412 and a complementary threaded female portion 418 disposed on the distal end of the proximal portion 414. When the male and female portions 416 and 418 of the coupling mechanism engage, a smooth transition between the distal and proximal portions 412 and 414 is provided. In this embodiment of the invention, the length of the distal portion 412 should be approximately 50 inches so that the distal portion 412 can be threaded over the guidewire first, allowing the guidewire to exit the proximal end of the distal portion 412 so that a physician can secure the guidewire while the distal portion 412 is advanced down a blood vessel. After the distal portion 412 is advanced to a desired location in the blood vessel, the proximal portion 414 is advanced over the proximal end of the guidewire until the female portion 418 reaches the male portion 416 of the distal portion 412 and is releasably attached to the proximal end of the distal portion 412.

In this disclosure, there is shown and described only exemplary embodiments of enhanced exchange catheters according to the present invention, but it is to be understood that the invention is capable of use in various other combination and environments and is capable of changes or modification within the scope of the inventive concept as expressed herein.

What is claimed is:

1. An improved exchange catheter comprising:

a flexible, elongate body configured to shield a guidewire from a guiding catheter having a proximal end, a distal end, a first port in the distal end at a distal extremity of the device, a second port spaced proximal to the distal end, a distal portion and a proximal portion, at least part of said distal portion having a radially enlarged section with a wall thickness and an outer diameter greater than said proximal portion and configured to facilitate slidable disposition within an inner lumen of a coronary guiding catheter;

a guidewire lumen in fluid communication with the first and second ports and configured to slidably receive a guidewire therein, and extending in at least said distal portion so that at least a section of said guidewire lumen is defined by the radially enlarged section of the distal portion of the body.

2. The exchange catheter of claim 1, wherein said proximal portion has a guidewire lumen formed therein having a diameter substantially equal to said distal portion guidewire lumen.

3. The exchange catheter of claim 1, wherein said distal portion is more flexible than said proximal portion.

4. The exchange catheter of claim 1, further comprising a guidewire-retaining member disposed on a proximal extremity of said proximal portion.

5. The exchange catheter of claim 1, wherein said proximal portion has an outer diameter of approximately 0.038 inch.

6. The exchange catheter of claim 1, wherein said distal portion has approximately a 4-French outer diameter.

7. The exchange catheter of claim 1, wherein said distal portion has a length of approximately 20 inches.

8. The exchange catheter of claim 1, further comprising a coupling mechanism disposed between said distal portion and said proximal portion for releasably interconnecting said distal portion and said proximal portion.

9. The exchange catheter of claim 8, wherein said coupling mechanism comprises:

the distal portion having a threaded proximal end; and the proximal portion having a complementary threaded distal end configured to be threadably engageable with said threaded proximal end of said distal portion.

10. The exchange catheter of claim 8, wherein said distal portion has a length of approximately 50 inches.

11. An exchange catheter system for use in the treatment of a coronary blood vessel lesion of a patient, comprising:

an exchange catheter configured to shield a guidewire from a guiding catheter, having a proximal end, a distal end, a first port within the distal end, a second port spaced proximal to the distal end, a distal portion positionable near said coronary blood vessel lesion and a proximal portion extendible outside said patient and a guidewire lumen formed within the distal portion and extending between the first and second ports;

a femoral sheath slidably disposed over the exchange catheter, with proximal and distal ends, a first port in the proximal end and a second port in the distal end and a lumen extending therein between the ports in the proximal and distal ends of the femoral sheath;

a tubular dilator longer than the femoral sheath slidably disposed within the lumen of the femoral sheath having proximal and distal ends, a port in the proximal end and a port in the distal end and having an inner lumen extending therein and in fluid communication with the ports in the proximal and distal ends of said dilator, the inner lumen having an inner diameter configured to facilitate advancement of the dilator over the exchange catheter;

a guidewire disposed within the guidewire lumen of the exchange catheter; and a secondary guiding catheter longer than the femoral sheath or tubular dilator, having a proximal end, a distal end, an inner lumen extending therein, a port in the proximal end, the port and the inner lumen having inner diameters which are configured to facilitate longitudinal displacement of the exchange catheter proximally from the secondary guiding catheter, and having an outer diameter configured to facilitate advancement of the secondary guiding catheter within the lumen of the femoral sheath.

12. The guiding catheter system of claim 11, wherein said exchange catheter proximal portion has a guidewire lumen formed therein communicating with said distal portion guidewire lumen.

13. The guiding catheter system of claim 12, further comprising a releasable guidewire-securing pin vise on the proximal end of said exchange catheter.

14. A method for exchanging a first guiding catheter with a second guiding catheter without disturbing guidewire poistion, said method comprising:

a) providing an exchange catheter comprising:
  a flexible, elongate body configured to shield a guidewire from a guiding catheter having a proximal end, a distal end, a first port in the distal end at a distal extremity of the device, a second port spaced proximal to the distal end, a distal portion and a proximal portion, at least part of said distal portion having a radially enlarged section with a wall thickness and an outer diameter greater than said proximal portion and configured to facilitate slidable disposition within an inner lumen of the first guiding catheter;
  a guidewire lumen in fluid communication with the first and second ports and configured to slidably receive a guidewire therein, and extending in at least said distal portion so that at least a section of said guidewire lumen is defined by the radially enlarged section of the distal portion of the body; and
  a coupling mechanism disposed between said distal portion and said proximal portion for releasably interconnecting said distal portion and said proximal portion, comprising a threaded proximal end on the distal portion and a complementary threaded distal end on the proximal portion configured to be threadably engageable with said threaded proximal end of said distal portion;

b) advancing said distal portion of said exchange catheter over a guidewire and through a first guiding catheter;

c) securing said guidewire;

d) advancing said proximal portion of said exchange catheter over a guidewire;

e) engaging said proximal with said distal portion;

f) removing said first guiding catheter;

g) advancing a second guiding catheter over said exchange catheter; and h) removing said exchange catheter from said second guiding catheter over the guidewire without removing the guidewire.

15. A system for exchanging a first coronary guiding catheter with a second coronary guiding catheter, comprising:

a) an exchange catheter having a flexible elongate shaft, a proximal end, a distal end, a port in at least the distal end at a distal extremity of the device, a proximal shaft portion, a distal shaft portion with a larger outer diameter than the proximal shaft portion, a guidewire lumen extending within at least the distal shaft portion and being in fluid communication with the port in the distal end and configured to slidably receive a guidewire therein, and the distal shaft portion having a wall portion which has a greater wall thickness than a wall portion of the proximal shaft portion and which radially extends continuously between the guidewire lumen and an exterior surface of the distal shaft portion, so that at least a section of said guidewire lumen is defined by said wall portion of the distal shaft portion, and which is configured to be slidably disposed within an inner lumen of a coronary guiding catheter; and b) a guidewire longer than the exchange catheter slidably disposed within the guidewire lumen of the exchange catheter and extending out the proximal and distal ends of the exchange catheter.

16. A method for exchanging a first guiding catheter with a second guiding catheter without disturbing guidewire position, said method comprising:

a) advancing over a guidewire and through a first guiding catheter an exchange catheter comprising:
  a flexible, elongate body configured to shield a guidewire from a guiding catheter having a proximal end, a distal end, a first port in the distal end at a distal extremity of the device, a second port spaced proximal to the distal end, a distal portion and a proximal portion, at least part of said distal portion having a radially enlarged section with a wall thickness and an outer diameter greater than said proximal portion and configured to facilitate slidable disposition within an inner lumen of the first guiding catheter;
  a guidewire lumen in fluid communication with the first and second ports and configured to slidably receive a guidewire therein, and extending in at least said distal portion so that at least a section of said guidewire lumen is defined by the radially enlarged section of the distal portion of the body;

b) withdrawing said first guiding catheter over said exchange catheter;

c) advancing a second guiding catheter over said exchange catheter and supporting the second guiding catheter with the radially enlarged section on the exchange catheter as the second guiding catheter is advanced thereon; and d) removing said exchange catheter from said second guiding catheter over the guidewire without removing the guidewire.

17. The method of claim 16, further comprising after withdrawing said first catheter and before advancing said second catheter:

advancing a dilator and a femoral sheath having a lumen configured to slidably receive the second guiding catheter over a proximal portion of said exchange catheter;

removing said dilator from said femoral sheath; and wherein advancing the second guiding catheter further comprises inserting the second guiding catheter in the lumen of the femoral sheath.

18. The method of claim 16, further comprising securing said guidewire to said exchange catheter with a guidewire retaining member on the exchange catheter, prior to removing said first guiding catheter.

* * * * *